United States Patent
Jones

(10) Patent No.: US 10,029,035 B2
(45) Date of Patent: Jul. 24, 2018

(54) SYSTEM, METHOD AND KIT FOR THE COLLECTION AND PROCESSING OF AMNIOTIC FLUID AND PLACENTAL ASPIRATE

(71) Applicant: G. Charles Jones, Missouri City, TX (US)

(72) Inventor: G. Charles Jones, Missouri City, TX (US)

(73) Assignee: PENSARA, INC, Richmond, TX (US)

( * ) Notice: Subject to any disclaimer, the term of this patent is extended or adjusted under 35 U.S.C. 154(b) by 511 days.

(21) Appl. No.: 14/638,574

(22) Filed: Mar. 4, 2015

(65) Prior Publication Data

US 2016/0256612 A1  Sep. 8, 2016

(51) Int. Cl.
*A61M 1/00* (2006.01)
*A61M 1/36* (2006.01)
*A61M 1/02* (2006.01)

(52) U.S. Cl.
CPC ........ *A61M 1/0005* (2013.01); *A61M 1/0259* (2013.01); *A61M 1/3693* (2013.01); *A61M 1/3695* (2014.02); *A61M 2202/0427* (2013.01); *A61M 2202/0462* (2013.01)

(58) Field of Classification Search
CPC .............. A61M 1/0005; A61M 1/3695; A61M 1/3693; A61M 1/0259; A61M 2202/0427; A61M 2202/0462
See application file for complete search history.

(56) References Cited

U.S. PATENT DOCUMENTS

| | | | | |
|---|---|---|---|---|
| 1,620,713 | A * | 3/1927 | Bell | F25B 39/04 165/111 |
| 4,957,629 | A * | 9/1990 | Smith | B01D 29/01 210/443 |
| 5,242,606 | A | 9/1993 | Braynin et al. | |
| 8,858,518 | B2 * | 10/2014 | Schafer | A61M 1/0005 604/317 |
| 9,096,827 | B2 * | 8/2015 | Meiron | C12N 5/0605 |
| 2014/0047986 | A1 | 2/2014 | Robinson | |
| 2014/0336600 | A1 * | 11/2014 | Harrell | C12N 5/0605 604/319 |

* cited by examiner

*Primary Examiner* — Tatyana Zalukaeva
*Assistant Examiner* — Gabriella Burnette
(74) *Attorney, Agent, or Firm* — Egbert Law Offices, PLLC

(57) ABSTRACT

Disclosed is a system for the collection, processing and reuse of amniotic fluid and placental aspirate at a C-section site. The system includes a canister positioned along the vacuum line through which the amniotic fluid and placental aspirate is suctioned. The canister has a coil whereby the heavier cellular components, including stem cells, platelets and growth factors, are separated coincident with the surgical procedure. The canister has a port whereby the heavier cellular material can be removed from the canister. The heavier cellular material can be then applied to the wound site of the cesarean section patient. The system disclosed allows for the processing of the amniotic fluid and placental aspirate to take place in the same room as the surgical procedure. A kit and method are also provided.

4 Claims, 5 Drawing Sheets

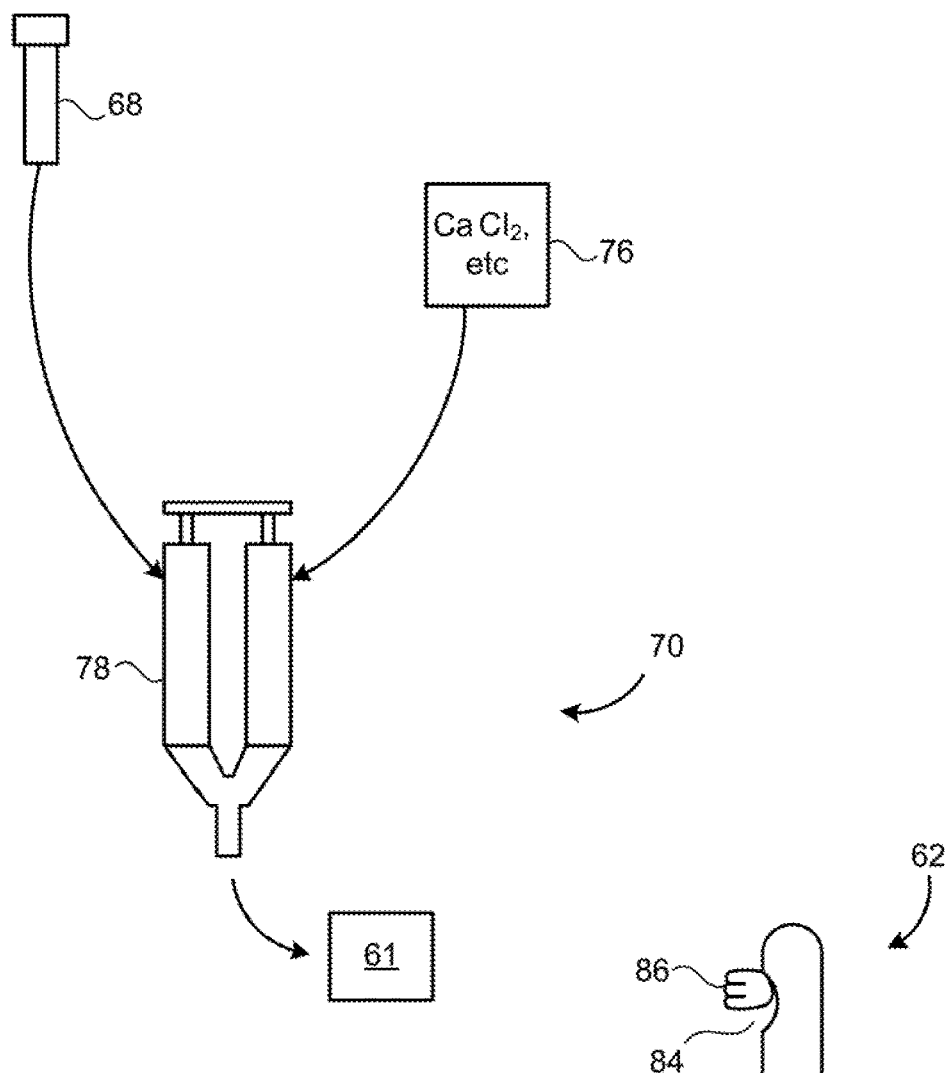

SYSTEM, METHOD AND KIT FOR THE COLLECTION AND PROCESSING OF AMNIOTIC FLUID AND PLACENTAL ASPIRATE

CROSS-REFERENCE TO RELATED APPLICATIONS

Not applicable.

STATEMENT REGARDING FEDERALLY SPONSORED RESEARCH OR DEVELOPMENT

Not applicable.

NAMES OF THE PARTIES TO A JOINT RESEARCH AGREEMENT

Not applicable.

INCORPORATION-BY-REFERENCE OF MATERIALS SUBMITTED ON A COMPACT DISC

Not applicable.

BACKGROUND OF THE INVENTION

1. Field of the Invention

The present invention relates to the field of the collection of amniotic fluid and placental aspirate. More particularly, the present invention relates to a system wherein amniotic fluid and placental aspirate can be collected at the cesarean section site, quickly processed, and reused as a medication for the patient. The present invention also relates to a kit for performing the system and method of the present invention.

2. Description of Related Art Including Information Disclosed Under 37 CFR 1.97 and 37 CFR 1.98

Caesarean section, or C-section, is the delivery of a baby through a cut in the mother's lower abdomen and the uterus. Today, it is one of the most frequently performed surgeries in the world, more commonly performed than gallbladder removal, hysterectomy, or tonsillectomy. A C-section may be lifesaving for the baby or the mother or both.

In a C-section, the first incision made is either a vertical incision in the middle of the abdomen, from below the navel down to the pubic bone, or a transverse or "bikini cut" incision, called an annesteil incision, from side to side just above the pubic hairline. The bikini cut incision is more common, because it heals better, has a shorter recovery time, and is more cosmetically acceptable. After going through the various layers of the abdominal wall and opening the bladder fold of peritoneum, the lower segment of the uterus is exposed. An incision is then made in the uterine wall. Usually, the incision is horizontal; this is preferred as it heals better and bleeds less. However, under some circumstances, it is necessary for the doctor to make a vertical incision in the uterus.

Recovery from a C-section generally takes longer than a vaginal delivery. During a C-section, the amniotic fluid and placenta are typically suctioned away or otherwise disposed of. This presents a missed opportunity, as amniotic fluid is known to have certain beneficial components, including growth factors. Placental aspirate also known to have beneficial components, including stem cells and platelets. The stem cells found in the placental aspirate could potentially be very useful, as the stem cells are less limited in their application than those of the most commonly available source of stem cells, bone marrow.

Typically, operating rooms are provided with a series of vacuum components, including a plurality of the vacuum suction lines whereby the liquid such as amniotic fluid can be removed from the surgical site and disposed of or used at a later time.

The separation of the components of liquid, most commonly blood, but is well-known. Numerous patents have issued in the past relating to separation of the components of blood, typically at utilizing centrifuges. U.S. Pat. No. 5,242,606 (the '606 patent) issued on Sep. 7, 1993 to Braynin et al. The '606 patent is an example of such a device for separating the plasma from whole blood. In the '606 patent, an analytical rotor is used having a sample application port in the upper surface thereof. Blood is introduced into the sample application port and metered into a metered chamber by capillary flow while the rotor remain stationary. Excess blood passes into an overflow chamber by capillary flow, either simultaneously with the metered flow or after opening of a vent in the overflow chamber. Subsequent rotation of the rotor causes metered blood in the metering chamber to flow into receiving chamber, typically a plasma separation chamber.

Cyclonic separation is also well known. For example, U.S. Patent Publication No. 2014/0047986, published on Feb. 20, 2014 to Robinson, describes systems and methods for salvaging red blood cells from patients during a surgical procedure. A system is described for cyclonically extracting blood from blood-soaked absorbent surgical materials such as surgical sponges, gauze, tape, and the like. The collected blood and fluids from these materials can be transferred to a cell salvage machine for harvesting viable red blood cells for autotransfusion.

Filtration of obstetrical fluids is also known, as well as filtration along a suction line. For example, refer to U.S. Pat. No. 4,957,629 (the '629 patent), issued on Sep. 18, 1992 Smith et al. The '629 patent describes a filter for obstetrical fluids and particulate matter having an enclosure containing a first chamber and a second chamber. The first chamber has a solid partition forming first and second cavities in the first chamber. The first cavity has an inlet and the second cavity has an outlet. The second chamber contains a filter and the edge of the partition is pressed against the surface of the filter.

The collection and reuse of amniotic fluid is also contemplated by others in the field. For example, refer to U.S. Patent Publication No. 2014/0336600 (the '600 publication), published on Nov. 13, 2014 to Harrell. The '600 publication describes a method for obtaining sterile amniotic fluid, as well as uses for such fluid. The '600 publication describes the use of a suction or a pump for collecting the amniotic fluid, as well as separation of cells such as growth factors and stem cells from the amniotic fluid. The '600 publication describes the separation of the growth factors and stem cells in a centrifuges remote from the collection site. The container utilizing in the '600 publication does not aid in the separation of the stem cells and growth factors. The process growth factors and stem cells collected using method of the '600 publication would not be suitable for or available for reuse as a medicine on the patient in which they were collected, as the separation of the cells occur to that location that time remote from the actual surgery. By the time the cells are separated and could possibly be reused, in all likelihood, the surgeon has since closed surgery site and moved on to the next procedure. Placental blood is also known to have stem cells and other beneficial components.

As such, there is a need for a system and method wherein stem cells and other beneficial cells from amniotic fluid and placental aspirate can be reused on the same patient so as to assist in the healing of the C-section wound.

It is an object of the present invention is to provide such a system and method to accomplish this goal.

It is another object of the present invention to provide a system for the collection of amniotic fluid which can be used with existing operating room equipment.

It is another object of the present invention to provide a system and method for the collection and processing of amniotic fluid and placental aspirate which allows for instant separation and reuse of the beneficial components of the amniotic fluid and placental aspirate.

It is another object of the present invention to provide a system for the collection and processing amniotic fluid and placental aspirate which is easy to use and does not require substantial amount of time in addition to the standard procedure.

It is another object of the present invention to provide a system and method for the collection and processing of amniotic fluid and placental aspirate which utilizes the amniotic fluid and placental aspirate speed healing and a cesarean section wound.

It is yet another object of the present invention to provide a system and method for the collection and processing of amniotic fluid and placental aspirate which utilizes an existing suction line to separate the beneficial components from the amniotic fluid and placental aspirate.

It is another object of the present invention to provide a kit having the components of the system described hereinabove.

These and other objects and advantages of the present invention will become apparent from a reading of the attached specification and appended claims.

BRIEF SUMMARY OF THE INVENTION

In one embodiment of the present invention, an apparatus for the collection and separation of cellular material from amniotic fluid and placental aspirate is provided. The apparatus includes a canister having an inlet and an outlet. The inlet is connected to a suction tube and the outlet connected to the vacuum line. A hollow coil is positioned in the interior of the canister. The hollow coil is in fluid communication with the inlet and outlet of the canister. A chamber is formed within the canister. A port is provided which is in communication with the chamber. Preferably, the port is positioned adjacent the inlet of the canister. In the present invention, the port may be suitable for receipt of a needle of a syringe therein.

In an embodiment of the present invention, the hollow coil has a teardrop-shaped cross section. In an embodiment of the present invention, the hollow coil has a first slot and a second slot adjacent the outlet. The first slot is connected to the outlet and a second slot opens to the chamber.

In another embodiment of the present invention, a second vacuum line may extend from an upper end of the chamber to the outlet of the canister. The another vacuum line is suitable for evacuating a liquid which accumulates in the outer chamber.

The present invention is also a kit for the collection, separation and use of cellular material from amniotic fluid and placental aspirate. The kit has a canister having a coil and a cellular accumulation chamber. In the kit of the present invention, the coil is preferably a hollow tubular coil. The cellular accumulation chamber has a port. The canister has an inlet and an outlet, the coil being connected to the inlet and to the outlet. The canister is suitable for attachment to a vacuum line. The kit also contains a syringe having a needle suitable for insertion into the port of the cellular accumulation chamber. Finally, a dual chambered applicator is provided which is suitable for receiving cellular material from the syringe.

The kit of the present invention may also include a coagulant or sealant in one chamber of the dual chambered applicator.

The kit of the present invention may also include a Yankauer suction tip suitable for connection to the vacuum line. The Yankauer suction tip may have a plurality of teeth thereon suitable for scraping a collection site.

In an embodiment of the present invention, the coil has a teardrop-shaped cross-section.

In an embodiment of the method of presentation, the coil has a slotted opening adjacent the outlet. One side of the slotted opening is in fluid communication with the outlet, while another side of the slotted opening is in fluid communication with chamber.

The present invention is also a method for collection and separation of cellular material from amniotic fluid and placental aspirate. The method includes the step of suctioning amniotic fluid from the cesarean section collection site using a vacuum line. Next, heavier cellular material is separated from the amniotic fluid using a canister having a coil therein. The canister is positioned along or in communication with the vacuum line. Finally, the heavier cellular materials are removed from the canister.

In the method of the present invention, the step of removing may include the steps of: providing a port on the canister, inserting a needle of a syringe into the port, and drawing the heavier cellular material into the interior of the syringe needle.

In the method of the present invention, another step may be provided wherein the heavier cellular material is applied to the cesarean section collection site. In this application, the step of applying includes the steps of mixing the heavier cellular material with a coagulant or sealant and applying the mixed heavier cellular material using an applicator. The coagulant or sealant may comprise calcium chloride.

The method of the present invention may also include the step of collecting placental aspirate from the cesarean section site. The placental aspirate is passed through the canister so as to separate the heavier cellular material, or to condense the placental blood. The condensed placental blood or heavier cellular material is then injected into the cesarean section collection site, preferably along the perimeter of the dermal cesarean section wound before or after suturing the site.

Importantly, in the method of the present invention, each of the steps is conducted in a single operating room coincident with the surgical procedure.

BRIEF DESCRIPTION OF THE SEVERAL VIEWS OF THE DRAWINGS

FIG. 5 is a schematic view showing the syringe and dual chambered applicator of the kit and method of the present invention.

FIG. 6 is a side view showing the Yankauer suction tip of one embodiment of the present invention.

DETAILED DESCRIPTION OF THE INVENTION

Figure 1:
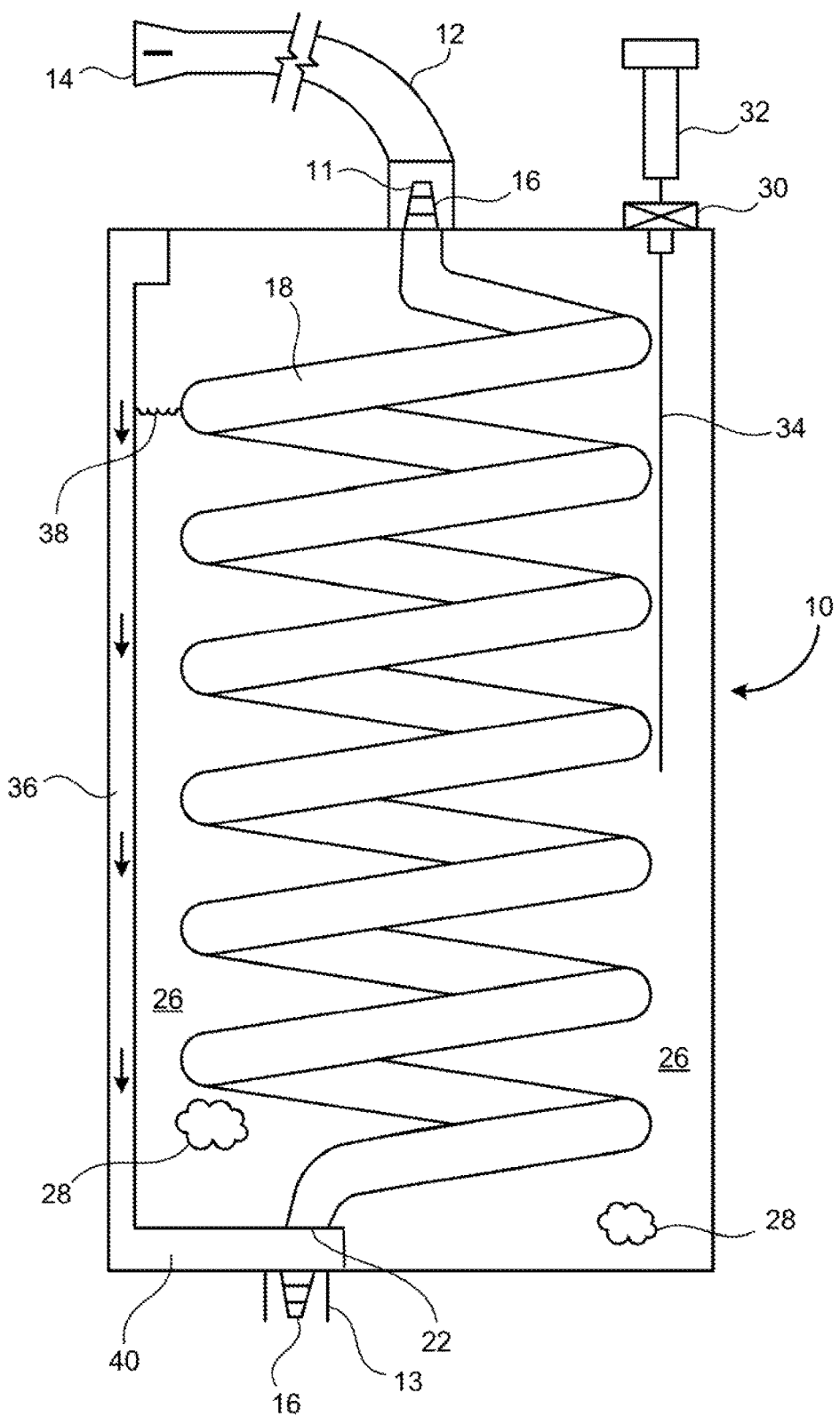
FIG. 1 is a schematic view showing the canister of the system of the present of the present invention.

Referring to FIG. 1, there is shown a sectional, schematic view of the canister 10 of the system of the present invention. The canister 10 is positioned along a vacuum line 12. The vacuum line 12 has a suction tip 14 at an end thereof. The vacuum line 12 is connected at connection 16 to the inlet 11 and outlet 13 of the canister 10 of the present invention. As will be described hereinafter below, amniotic fluid is collected using the suction tip 14 and introduced into the canister 10, wherein heavier cellular material is collected and the remaining amniotic fluid exits through a connection 16 adjacent the outlet 13 of the canister 10 and is disposed of or processed further. The inlet 11 and outlet 13 of the canister generally comprise the connections 16 and are in fluid communication with the interior of the canister 10.

As will be described hereinbelow, the canister 10 of the present invention may also be used to process placental blood, or placental aspirate, collected from the caesarian section site.

The canister 10 of the present invention preferably includes a coil 18. The coil 18 defines a pathway whereby the amniotic fluid or placental aspirate is urged into a cyclonic motion. A chamber 26 is defined by the interior of the canister 10 and the exterior of the coil 18. As such, preferably, the chamber 26 surrounds the coil 18.

The coil 18 is preferably a hollow tubular coil. The coil 18 extends in a spiral shape from the inlet of the canister towards the outlet. Adjacent the outlet 13 of the canister, the coil 18 has a slotted opening 22. As shown hereinbelow, the slotted opening 22 opens to both the outlet 13 of the canister 10 and to the chamber 26. The shape of the coil 18 urges heavier cellular material towards the outside of the coil, and thus, the heavier cellular material exits the slotted opening 22 on the side and enters the chamber 26.

This heavier cellular material 28 collects at a bottom of the chamber 26. Liquid can also accumulate within the chamber 26 as indicated by the liquid accumulation level 38 shown on the left side of the chamber 26. The remaining fluid exits the chamber 26 through the outlet 13 of the canister 10 and back into the vacuum line 12.

The canister 10 is provided with a port 30. The port 30 is preferably suitable for the receipt of a needle 34 of a syringe 32 (preferably 10 cc). The port 30 allows for access of the chamber 26, which functions as a cellular accumulation chamber. As shown in FIG. 1, the needle 34 can extend down into the chamber 26 so as to reach the accumulated cellular materials 28. The syringe 32 can then be used so as to remove the cellular materials 28 from the chamber 26. Preferably, the port 30 is provided adjacent to the inlet 11 of the canister 10. However, various other locations and ways of evacuating the accumulated cellular material 28 are possible within the concept of the present invention.

The canister 10 is generally cylindrical, and can be tilted such that the cellular materials 28 shown on the left side of the canister 10 in FIG. 1 can be allowed to move towards a location wherein the needle 34 of the syringe 32 can access the cellular material 28.

In one embodiment of the present invention shown in FIG. 1, a second vacuum line 36 is provided. The second vacuum line 36 generally runs from an upper end of the canister 10, in communication with the chamber 26, and down to the outlet 13 of the canister 10. The vacuum can be applied at location 40. The second vacuum line 36 is utilized so as to remove accumulated liquid 38 from the chamber 26. This excess liquid can be removed at location 40, or reintroduced into the vacuum line adjacent outlet 13.

Figure 2:
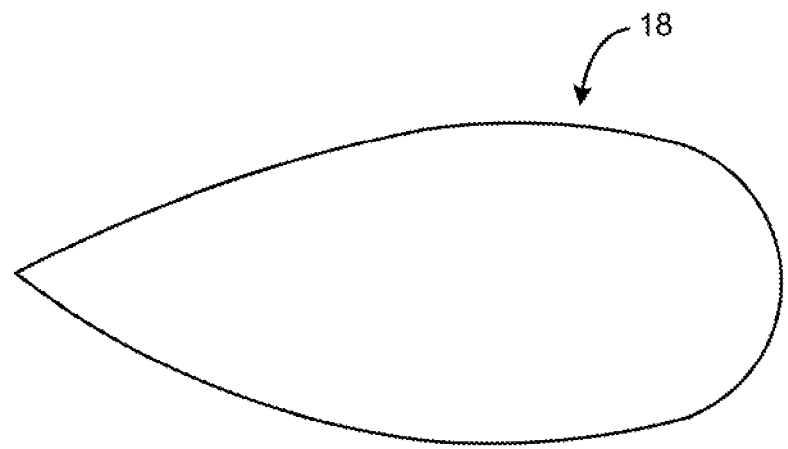
FIG. 2 is a sectional view of the coil of the canister of the system and method of the present invention.

Referring to FIG. 2, there is shown a sectional view of the coil 18 of a preferred embodiment of the present invention. In FIG. 2, it can be seen that the coil 18 has a teardrop-shaped cross-section. This shape aids in speeding the liquid through the interior of the coil 18, wherein the liquid is pushed to the outside of the teardrop shaped coil 18.

Figure 3:
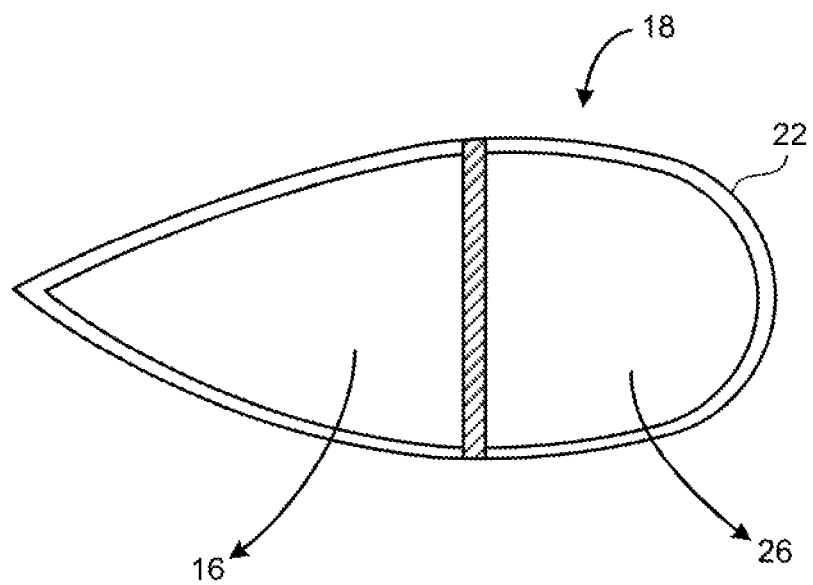
FIG. 3 is a sectional view showing the slotted opening of the coil of the present invention.

FIG. 3 shows a cross-sectional view of the coil 18 adjacent the slotted opening 22. As can be seen in FIG. 3, the slotted opening 22 has one side which is in fluid communication with the connection 16 of the outlet 13 of the canister 10. Another side of the slotted opening 22 of the coil 18 is in fluid communication with the chamber 26. The heavier cellular material passes through this opening into the chamber 26.

Figure 4:
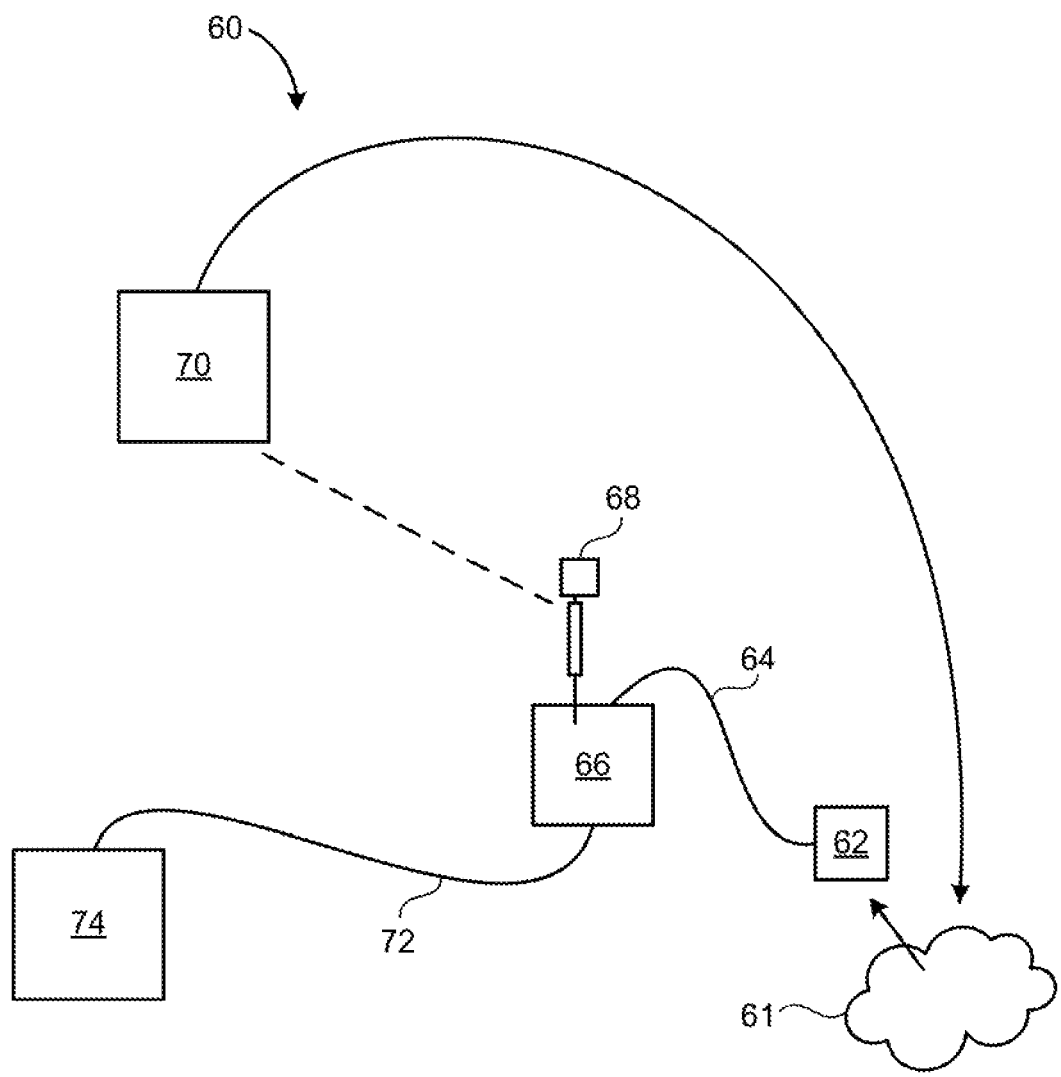
FIG. 4 is a schematic view showing the method of the present invention.

FIG. 4 shows a diagram of the system and method 60 of the present invention. A collection site 61 (or placenta) is shown in FIG. 4. A suction tip 62 of the system 60 of the present invention is applied to the collection site 61 so as to collect amniotic fluid. The amniotic fluid travels through the suction tip 62 and into the line 64. From the line 64, the amniotic fluid enters the canister 66 (as described hereinabove). In the canister 66, the separation of the heavier cellular materials, including growth factors, stem cells and platelets, is accomplished. The separation is accomplished coincident with the surgical process conducted at the collection site 61.

FIG. 4 also shows how the syringe 68 is inserted into the canister 66. The syringe 68 removes the heavier cellular material and to a mixing location 70. The location 70 is within the same operating room as the operation is being conducted. At 70, the heavier cellular material from the amniotic fluid is mixed with the coagulant or sealant (preferably 1-1.5 cc calcium chloride equal parts), and reapplied at the collection site 61, or the location of the wound. Specifically, the mixture is applied at the uterine and facial closure at the surgeon's discretion. The mixed cellular material and coagulant or sealant has the effect of a natural bandage on the wound site, speeding healing of the wound site. The anti-adhesive and antibacterial effects of the heavier cellular components aid in speeding the healing.

Because the separation of the beneficial components of the amniotic fluid occurs coincident with and in the same room as the C-section procedure, this allows for the immediate reuse thereof. As noted hereinabove, is the amniotic fluid were processed that remote location from the operating room, by the time such processing had occurred, the surgeon would likely have finished the procedure and closed the surgical incision. As such, the beneficial components of the amniotic fluid cannot be reused on the patient from which they were extracted.

Referring to FIG. 6, there is shown how the mixing at location 70 occurs. The syringe 68 is used to fill one chamber of the dual-chambered applicator 78. The second chamber is filled with a coagulant or sealant 76. The coagulant or sealant 76 can include calcium chloride. The dual-chambered applicator is then used to apply the mixed components path the wound or collection site 61.

FIG. 6 shows an example of a suction tip 62 in accordance with one embodiment the present invention. The suction tip 62 is a Yankauer suction tip, common in the art, but with the added benefit of a plurality of teeth 86. The suction tip 62 includes a tube 80 which connects at end 82 to the suction line in the operating room. There is an opening 84 through which liquid and other materials can be sectioned. Adjacent this opening 84 are the plurality of scraping teeth 86. A soft tip 88 is also provided. This suction tip 62 of the present invention is particularly suitable for a radial scraping of the placenta at the collection site. This radial scraping would allow for efficient and effective removal of amniotic fluid, as well as the beneficial heavier cellular material from the site.

In one embodiment of the present invention, the system for the collection and separation of the cellular material will be sold as a kit. The kit would necessarily include the novel canister shown in FIG. 1, as well as the syringe and dual chambered applicator with the coagulant or sealant. Optionally, the kit could include the suction tip 62 as shown in FIG. 6, as the suction tip is particularly suitable for the purposes of the kit.

The method of the present invention, as described herein, would comprise the following steps: (1) suctioning amniotic fluid from the cesarean section collection site using a vacuum line; (2) separating heavier cellular material from the amniotic fluid using a canister having a coil therein, the canister being positioned along in communication with the vacuum line; and (3) removing the heavier cellular material for the canister. The step of removing includes providing the port on the canister, inserting a syringe needle into the port, and drawing the heavier cellular material into the interior of the syringe needle. The heavier cellular material may be applied to the cesarean section collection site/wound. Prior to applying, the heavier cellular material may be mixed with the coagulant or sealant, such as calcium chloride, and then applied using an applicator. Importantly, the steps of the method of the present invention are each conducted in a single operating room where the C-section is being performed.

Figure 7:
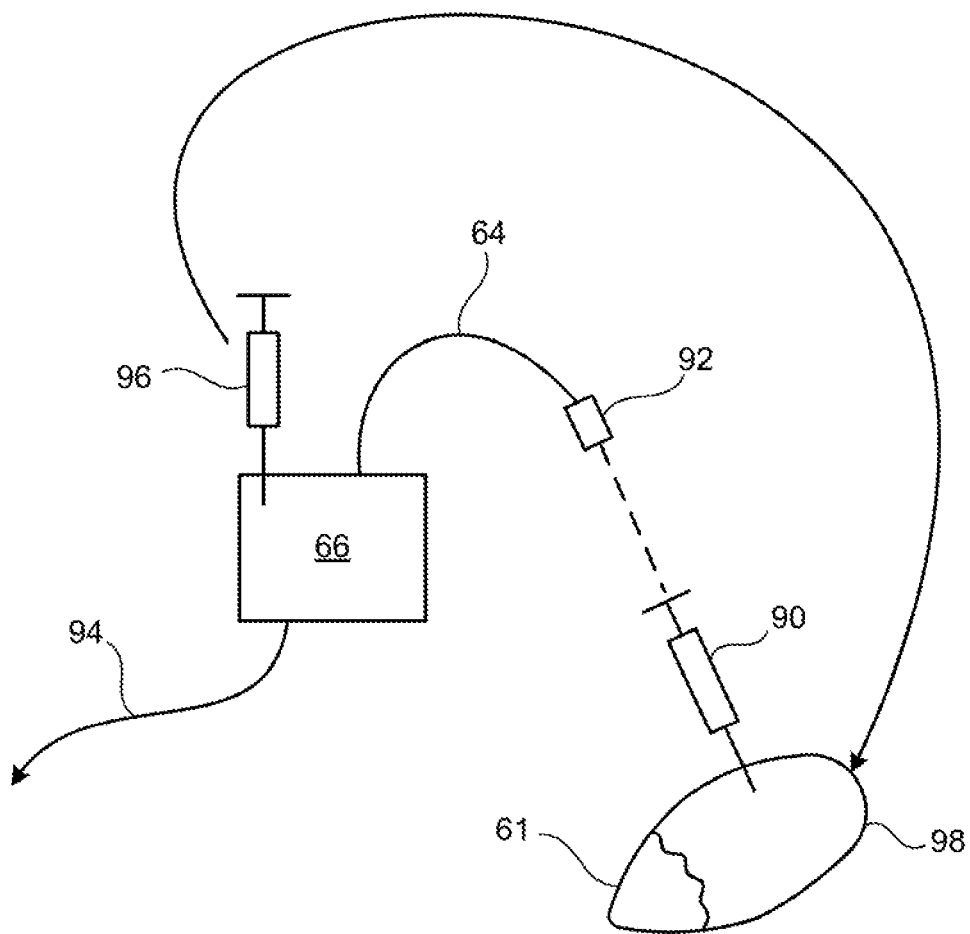
FIG. 7 is a schematic view showing additional steps in the system and method of the present invention wherein placental aspirate is collected, processed and reused.

The present invention may also be utilized to collect, process and reuse placental blood or placental aspirate from the collection site. FIG. 7 shows a schematic view of the placental aspirate collection and processing. Referring to FIG. 7, it can be seen how a second syringe 90 is utilized to draw up placental aspirate from the main vessels and arteries on the fetal placenta side of the placenta. The placenta is shown in FIG. 7 as reference numeral 61. Preferably, the second syringe 90 is a 30 cc syringe. The syringe 90 is then connected to a suction tip 92 so as to draw the collected placental aspirate into the line 64. The line 64, as shown in the previous figures, leads to the canister 66, where the placental aspirate is processed in the manner that the amniotic fluid was processed as described hereinabove.

Line 94 shows that how the resulting liquid is reused or disposed of. In FIG. 7, it can be seen how a third syringe 96, via a port in the cannister 66, is used to draw up the condensed placental blood, or heavier cellular materials of the placental aspirate therein. Preferably, the third syringe 96 is a 10 cc syringe. The third syringe 96 is then used to spot inject the process condensed placental aspirate along the perimeter 98 of the dermal caesarian section wound before after suturing of the wound Use of the process condensed placental aspirate on the wound further promotes reduced healing time, reduced scarring and increases the antibacterial defense in that area. Collectively, the processing and reuse of the amniotic fluid and placental aspirate should dramatically improve the patient's healing experience.

In a kit in accordance with the embodiment of the present invention wherein placental aspirate is collected, processed and reuse, the kit can further include the second and third syringes is 90 and 96, as well as a separate canister 66, if desired. The kit is importantly sterile such that it can be immediately used by the surgeon in the operating room.

Use of the system and method for the present invention allows for substantially decreased healing time for women undergoing a C-section. Because the processing of the amniotic fluid and placental aspirate occurs coincident with the C-section procedure, there is little extra time necessary in order to provide this natural, healing bandage and injection. As such, surgeons, who are very busy, would likely be willing to use a system and method of the present invention, as a relatively insignificant amount of time is needed to perform it.

The foregoing disclosure and description of the invention is illustrative and explanatory thereof. Various changes in the details of the illustrated construction can be made within the scope of the appended claims without departing from the true spirit of the invention. The present invention should only be limited by the following claims and their legal equivalents.

I claim:

1. A method for collection and separation of cellular material from amniotic fluid and placental aspirate comprising the following steps:
    coincident with a caesarian section procedure, suctioning amniotic fluid from a caesarian section collection site using a vacuum line;
    separating heavier cellular material from the amniotic fluid using a canister having a coil therein, wherein the coil has a tear drop shaped cross-section, said canister being positioned along or in communication with said vacuum line;
    removing said heavier cellular material from said canister;
    mixing said heavier cellular material with either of a coagulant or a sealant; and
    applying the mixed heavier cellular material to said caesarian section collection site using an applicator, wherein each of the steps are conducted in a single operating room.

2. The method of claim 1, said step of removing comprising:
    providing a port on said canister;
    inserting a syringe needle into said port; and
    drawing said heavier cellular material into an interior of said syringe needle.

3. The method of claim 1, said coagulant or sealant comprising calcium chloride.

4. The method of claim 1, further comprising the following steps:
    collecting placental aspirate;
    passing the collected placental aspirate through said canister so as to separate heavier cellular material from the passed placental aspirate; and
    injecting the heavier cellular material from the passed placental aspirate into said caesarian section collection site.

* * * * *